United States Patent [19]
Oda et al.

[11] Patent Number: 5,405,986
[45] Date of Patent: Apr. 11, 1995

[54] CATALYST AND METHOD FOR PRODUCING CARBONIC DIESTERS

[75] Inventors: Shingo Oda; Mitsuru Ohno, both of Himeji, Japan

[73] Assignee: Daicel Chemical Industries, Ltd., Osaka, Japan

[21] Appl. No.: 185,020

[22] Filed: Jan. 24, 1994

[30] Foreign Application Priority Data

Jan. 22, 1993 [JP] Japan .................. 5-027288

[51] Int. Cl.$^6$ ............................................. C07C 69/96
[52] U.S. Cl. ................................. 558/270; 558/271; 558/272; 558/273; 558/274; 558/277
[58] Field of Search ................. 538/270, 274, 275, 277

[56] References Cited

U.S. PATENT DOCUMENTS

| | | |
|---|---|---|
| 4,105,674 | 8/1978 | De Thomas et al. |
| 4,370,275 | 1/1983 | Stammann et al. ............... 558/260 |
| 4,483,998 | 11/1984 | Sanderson et al. |
| 4,604,242 | 8/1986 | Harley et al. |
| 5,171,874 | 12/1992 | Smith et al. ........................ 558/277 |

FOREIGN PATENT DOCUMENTS

| | | |
|---|---|---|
| 19271 | 2/1970 | Japan . |
| 8020 | 2/1981 | Japan . |
| 8816 | 3/1986 | Japan . |
| 43338 | 9/1986 | Japan . |

OTHER PUBLICATIONS

WO 87/07601, 17 Dec. 1987, PCT/US87/01309, Filed Jun. 5, 1987 Curnutt, Gerald L.

*Primary Examiner*—Joseé G. Dees
*Assistant Examiner*—Dwayne C. Jones
*Attorney, Agent, or Firm*—Cushman, Cushman & Darby

[57] ABSTRACT

A catalyst for synthesizing a carbonic diester includes at least one copper compound selected from among copper oxides, copper hydroxides, a salt of copper with a weak acid consisting of the elements other than halogen such as copper borates, and complexes or complex salts consisting of the elements other than halogen and formed with copper or a copper compound a and ligand. The catalyst has a high activity, a high reaction selectivity and excellent stability with a minimal risk of corroding equipment. The catalyst can include, as a co-catalyst component, a platinum-group metal such as palladium or a halogen-free platinum-group metal compound such as palladium acetate. The catalyst component may be supported on a carrier, for example, an activated carbon. A carbonic diester is advantageously produced by allowing an alcohol to react with carbon monoxide and oxygen in the presence of the catalyst. The corrosion due to the catalyst is considerably inhibited so that a dimethyl carbonate can be produced with an excellent stability for a long duration.

18 Claims, No Drawings

CATALYST AND METHOD FOR PRODUCING CARBONIC DIESTERS

FIELD OF THE INVENTION

The present invention relates to a catalyst for synthesizing carbonic diesters and to a method of producing a carbonic diester which comprises allowing the corresponding alcohol to react with carbon monoxide and oxygen in the presence of the catalyst.

BACKGROUND OF THE INVENTION

Carbonic diesters are compounds of value as automotive gas additives and organic solvents or as reactants, replacing phosgene, in the production of various carbonates, carbamates, urethanes and fine chemicals such as drugs and agrochemicals.

For the commercial production of a carbonic diester, generally the corresponding alcohol is allowed to react with phosgene. However, this known technology demands the use of phosgene having a great toxic potential and, moreover, the reaction of the alcohol with phosgene gives rise to a large quantity of hydrochloric acid which is a highly corrosive substance.

Therefore, a technology has been proposed for producing a carbonic diester without the use of phosgene which comprises allowing the corresponding alcohol to react with carbon monoxide and oxygen in the presence of a catalyst. The catalyst used for this purpose can be classified into two major categories, i.e. the palladium catalyst including a compound of palladium as the main catalyst component and the copper catalyst including a compound of copper as the main catalyst component.

The reaction using the palladium catalyst is described in Japanese Patent Publication Nos. 8816/1986 and 43338/1986. According to this technology, a palladium compound as the main catalyst component is used in combination with a copper compound and an alkali metal compound. The reaction conducted in the presence of a copper catalyst is described in Japanese Patent Publication No. 8020/1981. According to this technology, copper halides and the like are used as catalyst. And these reactions mentioned above are conducted in a liquid phase at a high pressure.

However, since the reaction liquid medium containing such a catalyst, irrespective of whether it is a palladium catalyst or a copper catalyst, is highly corrosive, the reaction must be conducted in a pressure-resistant reactor having an anticorrosive lining made of e.g. glass or a baked-on type enamel. Therefore, since there is an upper limit to the size of a pressure-resistant reactor having such an anticorrosive lining that can be fabricated, it is difficult to produce a carbonic diester containing such a catalyst on a commercial scale.

To obviate this corrosion problem associated with a liquid-phase reaction, a technology has been proposed for producing a carbonic diester which comprises allowing the corresponding alcohol to react with carbon monoxide and oxygen in a gas phase in the presence of a solid catalyst. For example, JP-A-503460/1988 corresponding to WO87/07601 discloses a production process which comprises allowing all the reactants to react in a gas phase using a catalyst comprising cupric chloride supported on a solid support by an impregnation technique.

This technology, however, has a disadvantage that the catalyst tends to be deteriorated since chlorine is eliminated from the catalyst in the course of the reaction. In other words, since the reaction of producing a carbonic diester which comprises allowing an alcohol to react with carbon monoxide and oxygen is a redox reaction, the valency of copper transfers between monovalent and divalent. Therefore, when cupric chloride is used as a catalyst component, chlorine is liable to be eliminated from the catalytic system corresponding to the equilibrium between cations and anions. Further, the technology has a drawback that atacamite [$Cu_2(OH)_3Cl$] is produced by reacting by-product water with copper chloride, and an excess amount of chlorine is eliminated from the system and the deterioration of the catalyst is enhanced. Additionally, according to this technology, a highly anti-corrosive reactor is still required, since chloride eliminated from the system causes the corrosion of the equipment. Meanwhile, in the above-mentioned literature, a method of regenerating the catalyst in order to supply the eliminated amount of chlorine to the system is proposed. The corrosion of the reactor, however, is still a disadvantage of the technology, because hydrogen chloride is used in the regeneration of the catalyst.

In these technologies for producing a carbonic diester, irrespective of whether it is a liquid phase reaction or a gas-phase reaction, there are the corrosion of the equipments and the deterioration of the catalysts and these drawbacks add up to a considerable disadvantage in the mass production of a carbonic diester.

SUMMARY OF THE INVENTION

Therefore, an object of the present invention is to provide a catalyst for synthesizing a carbonic diester not only having a high activity, a high reaction selectivity and an excellent stability, but also a significantly minimized risk of corrosion.

It is another object of the invention to provide a method of producing a carbonic diester which involves a minimal risk of corrosion, is conducive to high and stable production, and is capable of providing for a high selectivity for the carbonic diester for a long period of time.

The inventors of the present invention found, after an energetic research endeavor to accomplish the above-mentioned objects, that when an alcohol is allowed to react with carbon monoxide and oxygen using a catalyst containing at least one copper compound selected from the group consisting of copper oxides, copper hydroxides, a salt of copper with a weak acid consisting of the elements other than halogen, and complexes or complex salts formed with copper or a copper compound consisting of the elements other than halogen and a ligand consisting of the elements other than halogen, the corrosion of the equipment and the deterioration of the catalyst are remarkably suppressed, so that the desired carbonic diester can stably be produced with a very high yield and selectivity for a long duration. The present invention has been brought into being on the basis of the above finding.

Thus, the present invention provides a catalyst for synthesizing a carbonic diester which comprises at least one copper compound as a catalyst component selected from the group consisting of copper oxides, copper hydroxides, a salt of copper with a weak acid consisting of the elements other than halogen, and complexes or complex salts formed with copper or a copper compound consisting of the elements other than halogen and a ligand consisting of the elements other than halogen.

The catalyst for synthesizing a carbonic diester just mentioned above may further comprise, for example, a platinum-group metal or a platinum-group metal compound consisting of the elements other than halogen. Further, the catalyst component of the catalyst may be supported on a carrier (support), for instance, an activated carbon.

The present invention also provides a method of producing a carbonic diester which comprises allowing an alcohol to react with carbon monoxide and oxygen in the presence of said catalyst. The reaction may be carried out in a liquid phase or in a gas phase.

DETAILED DESCRIPTION OF THE INVENTION

It should be understood that the term "consisting of the elements other than halogen" as used in this specification means containing no halogen atom as the molecular constituent elements.

The copper oxides include cuprous oxide, cupric oxide and the like. The copper hydroxides includes cuprous hydroxide, cupric hydroxide and so on.

The weak acid mentioned above may vertically be any weak acid which consists of the elements other than halogen. Thus, the weak acid may be exemplified as carboxylic acids such as formic acid, acetic acid, propionic acid, oxalic acid, malonic acid, lactic acid, malic acid, citric acid, tartaric acid, benzoic acid, toluic acid, salicylic acid, phthalic acid, and nicotinic acid; phenols such as phenol and catechol; inorganic weak acids such as carbonic acid, boric acid including orthoboric acid, metaboric acid and tetraboric acid, hypoboric acid, peroxyboric acid, silicic acid and phosphoric acid; a metal oxo acid such as aluminic acid, vanadic acid, stannic acid, antimonic acid, bismuthic acid, molybdic acid and tungstic acid; and so on. As the carboxylic acids, carboxylic acids having 2 to 8 carbon atoms are preferred.

The acidity of the weak acid is not so critical, but the logarithm value of the inverse of the dissociation constant of the weak acid in an aqueous solution at 25° C. (pKa value) is usually not less than zero, and preferably not less than 2.

The complexes or complex salts formed with copper or a copper compound include complexes formed with copper or the copper compound as above and a ligand, and salts thereof. As the ligand, there may be mentioned, for example, boron compounds including nitrogen-containing boron compounds such as boron nitride, borazane, borazene, borazine, borazol, borinoaminoborine, boron amide and boron imide, and borane derivatives such as $BH_4$ (tetrahydroborato), $B_3H_8$ (octahydrotriborato), a compound shown by the formula $(CH_2=CH)_2BOBz$ wherein Bz represents benzyl group; amines such as methylamine, dimethylamine, trimethylamine, triethylamine, ethylenediamine and diethylenetriamine; nitrogen-containing heterocyclic compounds such as pyridine, pyrrolidine, piperidine, pyrimidine, imidazole, picoline, quinoline, isoquinoline, 1,10-phenanthroline, quinazoline, 2,2'-dipyridyl, 4,4'-dipyridyl, picolinic acid and nicotinic acid; amides such as acetamide and N-methylpyrrolidone; organophosphorus compounds including phosphines such as triphenylphosphine and dimethylphenylphosphine, phosphites such as trimethylphosphite and triphenylphosphite, and phosphorus triamides such as hexamethylphosphorus triamide; nitriles such as acetonitrile and benzonitrile; isonitriles such as methylisocyanide and phenylisocyanide; thiourea; and the like. Said copper or copper compound and the ligand can be used in the form of complex or in the form of mixture of the both.

The valency of the copper in these copper compounds to be contained in the catalyst is not critically restricted, but the copper may preferably be monovalent or divalent and more preferably divalent. These copper compounds can be used independently or in combination.

The preferred examples of the copper compounds include copper hydroxides, copper oxides, salts of copper with a carboxylic acid, one of phenols, a metal oxo acid or an inorganic weak acid, a complex or a complex salt formed with copper or a copper compound and a boron compound and so on. Among them, copper hydroxides such as cuprous hydroxide and cupric hydroxide; salts of copper with a carboxylic acid having 2 to 8 carbon atoms including copper acetates such as cuprous acetate and cupric acetate; copper borates such as copper metaborate and cupric borate; a complex or a complex salt formed with copper or a copper compound consisting of the elements other than halogen and a ligand such as a nitrogen-containing boron compound and borane derivative consisting of the elements other than halogen can be advantageously used, with copper borates being the copper compound of choice.

The catalyst of the present invention may comprise the above-mentioned copper compound as the catalyst component independently, as well as it may contain, as a co-catalyst component, a platinum-group metal or a platinum-group metal compound consisting of the elements other than halogen.

The platinum-group metal include palladium, platinum, rhodium, ruthenium, iridium and others. Palladium and the like can be preferably used among these metals.

The platinum-group metal compound may virtually be any compound as far as containing no halogen atom as the molecular constituent atom. As examples of the platinum-group metal compound, there may be mentioned salts of platinum-group metal with one of the above exemplified carboxylic acids, salts with one of the inorganic weak acids as above, oxides, hydroxides, complexes, and salts with a strong acid such as sulfuric acid and nitric acid. The preferred platinum-group compound is a salt with one of the carboxylic acids, particularly a salt of palladium with one of the carboxylic acids, with palladium acetate being the compound of choice. These platinum-group metal and platinum-group metal compound consisting of the elements other than halogen can be employed independently or in combination.

When said platinum-group metal and the like is used as the co-catalyst component, an improved catalytic activity can be realized.

The amount of the co-catalyst component can be selected from the suitable range depending on the catalytic activity, economic factors and other factors, thus being, per mole of the copper compound, usually about 1 mole or less, preferably about 0.1 mole or less and more preferably about 0.0001 to 0.05 mole. Since such platinum-group metal compound and the like can exhibit an excellent efficiency even when used in a small amount and is usually high-costed, a large quantity of the compound is not required to be used.

The catalyst of the invention can further comprise other compounds containing no halogen atom as the molecular constituent atom such as transition metal compounds, alkali metal compounds, alkaline earth metal compounds, boron compounds e.g. boric acid including orthoboric acid, metaboric acid and tetraboric acid, a salt with boric acid, boryl compounds such as boryl acetate, boryl phosphate and boryl arsenate, boric acid esters and the like. Among these compounds, boron compounds as above can advantageously be employed.

In the present invention, the catalyst may frequently contain boron atom in the catalyst component. Said boron atom may compose the main catalyst component with copper atom or be included in other component. When use is made of such catalyst containing boron atom, a specifically improved activity and selectivity can be obtained without the corrosion of the equipment.

Thus, the catalyst may preferably be contain boron compounds consisting of the elements other than halogen, such as copper borates; nitrogen-containing boron compounds; borane derivatives; boric acids; hypoboric acid; peroxoboric acid; boryl compounds; boric acid esters, and others as above. These boron compounds can be used independently or in combination.

Typical examples of the catalyst include a catalyst containing, as the catalyst component, a copper-containing boron compound such as salt of copper with an inorganic weak acid containing boron atom such as a copper borate or a complex or a complex salt formed with copper or a copper compound and a ligand containing boron atom such as a nitrogen-containing boron compound or a borane derivative.

The catalyst of the present invention may be a solid catalyst such as powder of the catalyst component as it is, or a liquid wherein the catalyst component is dispersed or dissolved in a suitable solvent. Further, a catalyst compression-molded with an adequate binder can also be employed.

Furthermore, the catalyst of the invention can be a supported catalyst wherein the catalyst component is supported on a proper carrier such as an activated carbon, alumina, silica gel, magnesia, titania, vanadia and zirconia.

The specific surface area of the carrier is not critical, thus being usually about 10 m²/g or more, and preferably about 100 to 3,000 m²/g.

Typically preferred example of the carrier include an activated carbon or the like. The specific surface area of the activated carbon may be, for example, about 500 m²/g or more, preferably about 700 to 3,000 m²/g, and more preferably about 900 to 3,000 m²/g. The mean pore size of the activated carbon may not be specifically restricted, thus being preferably about 10 to 100 Å and more preferably about 10 to 50 Å.

When a supported catalyst is employed, the supporting amount of the catalyst component is, based on the weight of the carrier, usually about 0.5 to 60% by weight, preferably about 1 to 40% by weight, and more preferably around the saturated absorption amount, for example in case of the activated carbon, about 2 to 20% by weight.

The supported catalyst can be produced in a conventional manner. Practically preferable technique is a technique where a precursor of the catalyst component or the catalyst component can be extensively dispersed to be supported on a carrier. The supporting procedure may be conducted in a single step or in a multiple of steps.

When use is made of a catalyst component soluble in a solvent, e.g. water, such as copper acetates or palladium acetates, the catalyst component may be dissolved in such a solvent and the resulting solution can be adsorbed or supported on a carrier.

When a catalyst component being slightly or sparingly soluble in a solvent such as copper borates, copper hydroxides and copper phosphate is employed, said catalyst component can be supported on a support as a combination of two or more soluble compounds corresponding to the precursors of said catalyst component. For instance, supporting can be conducted by adsorbing or impregnating a combination of a copper sulfate and a boric acid or a sodium borate, a copper sulfate and sodium hydroxide, a copper nitrate and sodium phosphate, or other combinations consequently on a carrier and, if required, washing the impregnated carrier.

Further, the catalyst supporting a copper oxide can be prepared as follows. For example, a salt of copper is first supported on a carrier, and the resulting substance may be treated with a high concentration and excess amount of sodium hydroxide, or submitted to thermal decomposition. It can also be prepared by oxidizing a carrier supporting copper metal. When a plural of the catalyst components are used, they may be supported simultaneously or in turn.

The catalyst of the present invention wherein at least one copper compound selected from the group consisting of copper oxides, copper hydroxides, a salt of copper with a weak acid consisting of the elements other than halogen and complexes or complex salt formed with copper or a copper compound consisting of the elements other than halogen and a ligand consisting of the elements other than halogen is used as the catalyst component, has a high catalytic activity, a high reaction selectivity and an excellent stability. In addition, it has a minimal risk of causing corrosion with production of highly corrosive by-products being significantly inhibited. Therefore, the corrosion of the equipment is minimized to enable a mass production run so that carbonic diesters (e.g. dimethyl carbonate) can stably be produced with a remarkably improved yield and selectivity for a prolonged duration.

According to the method of the present invention, an alcohol is allowed to react with carbon monoxide and oxygen in the presence of said catalyst.

The examples of the alcohol mentioned above include saturated aliphatic alcohols such as methanol, ethanol, 1-propanol, 2-propanol and 1-butanol; unsaturated aliphatic alcohols such as allyl alcohol; alicyclic alcohols such as cyclohexanol; aromatic alcohols such as benzyl alcohol and phenol; and polyhydric alcohols such as ethylene glycol and polyethylene glycol. The term "aromatic alcohol" is used herein to include a variety of phenols containing a phenolic hydroxyl group.

The preferred alcohol is a saturated or unsaturated monohydric alcohol, such as alcohols of about 1 to 6 carbon atoms. The particularly preferred alcohol includes methanol and ethanol, with methanol being the alcohol of choice.

Carbon monoxide and oxygen as reactants need not be a high-purity gas but can be used as diluted with an inert gas such as nitrogen, argon, helium, carbon dioxide and so on. In such cases, air may be substituted for oxygen. Furthermore, by-product carbon dioxide gas formed in the course of reaction may be recycled in the reaction system.

The method of the present invention can be applied to a liquid-phase reaction or a gas-phase reaction.

When the carbonic diester is produced by a liquid-phase reaction, the reaction may be conducted in the absence of any solvent or in the presence of an inert solvent. As examples of said solvent, there may be mentioned ketones such as acetone, methyl ethyl ketone and cyclohexanone; ethers such as diethyl ether, dibutyl ether, dimethoxyethane, dioxane and tetrahydrofuran; carboxylic acids such as formic acid, acetic acid and propionic acid; esters of carboxylic acids such as methyl acetate, ethyl acetate, isopropyl acetate, butyl acetate, amyl acetate, cellosolve acetate and ethyl propionate; amides of carboxylic acids such as N,N-dimethylformamide; nitriles such as acetonitrile, propionitrile and benzonitrile; aliphatic hydrocarbons such as hexane and octane; alicyclic hydrocarbons such as cyclohexane; aromatic hydrocarbons such as benzene, toluene, xylene and ethyl benzene; halogenated hydrocarbons such as carbon tetrachloride, chloroform, dichloromethane and 1,2-dichloroethane; the objective carbonic diester; and the like. Further, the material alcohol can also be employed as the solvent. These solvents can be used independently or in combination.

When the reaction is conducted in a liquid phase, any catalyst as mentioned above can be employed. Specifically preferred catalyst includes copper borates, copper hydroxides, copper oxides, a salt of copper with a metal oxo acid, a complex formed with copper or a copper compound and a boron compound consisting of the elements other than halogen and the like. Copper borates or a complex formed with copper or a copper compound and a nitrogen-containing boron compound or a borane derivative consisting of the elements other than halogen can advantageously be used among others.

As the catalyst, powder of the catalyst component or others intact as well as a supported catalyst can be used. Further, the catalyst may be produced in the reaction system by adding a compound capable of being the precursor of the catalyst component.

The amount of the catalyst to be used can be selected from the range depending on reaction rate, simplicity of operation of after-treatment and economic factors. Thus, the proportion of the catalyst in the reaction liquid medium, frequently being a solution or dispersion, is for example about 0.001 to 5 g atoms/liter, preferably about 0.01 to 3 g atoms/liter and more preferably about 0.1 to 2.5 g atoms/liter, in terms of atomic copper.

The reaction temperature may range usually about from 20° to 200° C. and preferably about from 80° to 150° C. When the reaction temperature is excessively low, the reaction rate may be significantly reduced, on the contrary, when the reaction temperature is excessively high, it may frequently give rise to side reactions.

The reaction pressure is generally about 1 to 200 atm and preferably about 1 to 60 atm, and the carbon monoxide partial pressure is, for instance, about 0.1 to 200 atm and preferably about 1 to 60 atm. The oxygen partial pressure is not critical but is generally selected from the range where an explosive mixture will not be formed. Thus, the oxygen partial pressure may for example be generally about 0.1 to 20 atm and preferably about 0.5 to 10 atm. As for the ratio of carbon monoxide and oxygen, carbon monoxide may be used about 1 to 100 moles per mole of oxygen.

Meanwhile, the method of producing a carbonic diester by a gas-phase reaction can be carried out into practice using any catalyst as mentioned above. Among them, in order to insure reducing the pressure loss of the reaction gases, removing reaction heat, improving the reaction rate or others, a solid catalyst, preferably a supported catalyst, especially a catalyst wherein the catalyst component is supported on an activated carbon can advantageously be used.

The gas-phase reaction can be carried out at a temperature of usually about 50° to 200° C., at a pressure of usually about 1 to 50 atm and with a space velocity of the material gas of, for example, about 10 to 100,000 $h^{-1}$. Regarding the composition of the feed gas flow to the reactor, the alcohol content may be about 1 to 50% by volume and the carbon monoxide content may vary about from 40 to 95% by volume, respectively based on the total volume of the alcohol, carbon monoxide and oxygen. The amount of carbon monoxide per mole of the material alcohol to be employed is usually about 0.1 to 1,000 moles and preferably about 0.2 to 100 moles. The using amount of oxygen per mole of the alcohol is usually about 0.001 to 2 moles and preferably about 0.01 to 1.5 moles.

The method of the invention can be conducted in practice by any system selected from a batch system, semi-batch system or continuous system. The desired carbon diester corresponding to the material alcohol can be obtained by treating resulting products in a conventional manner.

Thus, the catalyst for synthesizing a carbonic diester of the present invention has a high catalytic activity, a high reaction selectivity and an excellent stability, and in addition, has a minimal risk of causing the corrosion with production of corrosive by-products being remarkably inhibited.

In accordance with the production method of the invention, wherein such excellent catalyst as above is used, the corrosion of the equipment is minimized to enable a mass production run so that carbonic diesters (e.g. dimethyl carbonates) can stably be produced with a significantly improved selectivity and yield for a long period of time.

The following examples are intended to describe the present invention in further detail and should by no means be interpreted as defining the scope of the invention.

EXAMPLES

Example 1

Copper Borate Catalyst

Copper sulfate pentahydrate (4.7 g) was dissolved in 100 ml of water, and to the solution was added 40 g of activated carbon [trade name: Shirasagi C2X (mean pore size 17 Å), Takeda Chemical Industries, Ltd.]. The mixture was stirred for 1.5 hours at 50° C., followed by distilling off the solvent, and dried at 100° C. under reduced pressure.

The obtained activated carbon supporting copper sulfate was added to a solution prepared by dissolving 7.2 g of sodium borate decahydrate in 150 ml of water, and the above-mentioned procedure was otherwise repeated, that is, stirring, distilling off the solvent, and drying under reduced pressure were conducted. The resulting material was washed with water as far as sulfuric acid radical was not detected in washings then dried sufficiently at 100° C. under reduced pressure. Meanwhile, 1N aqueous solution of barium chloride was used for detecting sulfuric acid radical.

The catalyst supporting copper borate thus obtained was packed into a stainless steel tubular reactor, 27 mm in inside diameter and 450 mm long, to provide a 76 mm-deep catalyst bed. With the reaction temperature being set at 120° C., a mixed gas of $CO/O_2$/methanol=82/2/16 (by volume) was introduced at a space velocity of 500 $h^{-1}$ for 4 hours. During this time, the internal pressure of the tubular reactor was held at 7 $Kg/cm^2$ gauge. The reaction product gas emerging from the outlet of the reactor was condensed by cooling at $-70°$ C. The resulting condensate and the non-condensible gas were respectively analyzed by gas chromatography using the internal standard method and the absolute calibration method.

As a result, dimethyl carbonate was obtained at a rate of 0.4 mole/h per liter of the catalyst. The methanol-based selectivity for dimethyl carbonate was 90% and the selectivity for by-product methyl formate amounted to 9% on methanol-basis.

Example 2

Copper Borate Catalyst

The procedure of Example 1 was otherwise repeated except that a gaseous mixture of $CO/O_2$/methanol=88/1/11 (by volume) was fed to the tubular reactor at a space velocity of 200 $h^{-1}$ and the internal pressure of the tubular reactor was held at 20 $Kg/cm^2$ gauge.

As a result, dimethyl carbonate was obtained at a rate of 0.62 mole/h per liter of the catalyst and the methanol-based selectivity for dimethyl carbonate was 80%. The selectivity for by-product methyl formate amounted to 19% based on methanol.

Example 3

Copper Borate Catalyst

In 200 ml of water, was dissolved 12.48 g of copper sulfate pentahydrate and, separately, 19.7 g of sodium borate decahydrate was dissolved in 500 ml of water to prepare aqueous solutions. The aqueous solution of sodium borate was added to the aqueous solution of copper sulfate with stirring. The resulting precipitate was centrifuged, washed with water sufficiently as far as no sulfuric acid radical was detected in washings, and washed with acetone successively. The resulting precipitate was dried thoroughly under reduced pressure and milled fully with a mortar.

Using the copper borate-supporting catalyst thus obtained, the following procedure was conducted. A 300-ml capacity glass-lined autoclave equipped with a stirrer was charged with 50 ml of methanol containing 50 mmoles per liter of copper borate and the gas phase was substituted with carbon monoxide.

Subsequently, carbon monoxide was supplied to the autoclave at a pressure of 23 $Kg/cm^2$, then the reaction temperature was held at 135° C. for 10 minutes. After discharging the pressure, carbon monoxide and oxygen were fed to the autoclave respectively at pressures of 23 $Kg/cm^2$ and 2.0 $Kg/cm^2$, thus reaction was conducted at a temperature of 80° C. for 30 minutes. After cooling to room temperature, the reaction mixture and product gas were respectively analyzed by gas chromatography.

As a result, 0.1 mmole of dimethyl carbonate was obtained. By-production of carbon dioxide gas was not detected.

Example 4

Copper Acetate Catalyst

In 100 ml of water was dissolved 3.77 g of copper acetate and 40 g of the activated carbon used in Example 1 was added to the resulting solution. The mixture was stirred at 50° C. for 1.5 hours for adsorbing and supporting. The resulting material was dried by distilling off water at 50° C., and was dried at 130° C. for 18 hours in nitrogen gas stream to provide a copper acetate-supporting catalyst.

Using the catalyst thus obtained, the reaction procedure of Example 1 was otherwise repeated. As a result, dimethyl carbonate was produced at a rate of 0.50 mole/h per liter of the catalyst and the methanol-based selectivity for dimethyl carbonate was 93%. The selectivity of by-product methyl formate amounted to 5% based on methanol.

Example 5

Copper Acetate Catalyst

A 300-ml capacity glass-lined autoclave equipped with a stirrer was charged with 50 ml of methanol containing copper acetate in a proportion of 50 mmoles per liter, and the gas phase was substituted with carbon monoxide.

The reaction procedure of Example 3 was repeated and the resulting products were analyzed. Consequently, 3.0 mmoles of dimethyl carbonate was obtained and 1.6 mmoles of carbon dioxide gas was by-produced.

Example 6

Copper Hydroxide Catalyst

The copper sulfate-supporting activated carbon obtained in Example 1 was dipped in 1N aqueous solution of sodium hydroxide for 1.5 hours, and the supernatant was removed off. The resulting material was washed with water as far as the washings were not alkaline, and was dried at 130° C. under reduced pressure for 4 hours to provide a copper hydroxide-supporting catalyst.

The reaction procedure of Example 1 was repeated except for using the catalyst thus obtained. As a result, dimethyl carbonate was obtained at a rate of 0.21 mole/h per liter of the catalyst and the methanol-based selectivity for dimethyl carbonate was 90%. As a by-product, methyl formate was produced in the methanol-based selectivity of 9%.

Example 7

Copper Acetate-palladium Acetate Catalyst

Copper acetate and palladium acetate were dissolved in such a sufficient amount of water to be absorbed by activated carbon, and the activated carbon used in Example 1 was impregnated and supported with the solution in a porcelain dish. The resulting activated carbon was dried at 80° C. in nitrogen gas stream for 16 hours to provide a catalyst supporting 10% by weight of copper acetate and 0.2% by weight of palladium acetate.

The catalyst (15 ml) was packed into a tubular reactor of 15 mm in inside diameter, equipped with a thermometer tubular sheath of 6 mm in outside diameter. With the reaction temperature being held at 90° C., a mixed gas of $CO/O_2$/methanol/nitrogen=4.5/2.1/3.1/90.3 (by volume) was introduced at a rate of 180 normal liters per hour.

Consequently, 9% of methanol to be fed was converted to dimethyl carbonate and dimethyl carbonate was obtained at a rate of 0.74 mole/h per liter of the catalyst. The methanol-based selectivity and carbon monoxide-based selectivity for dimethyl carbonate were respectively 100% and 90%.

Comparative Example 1

Copper Sulfate Catalyst

The preparing procedure of Example 1 was otherwise repeated to obtain a copper sulfate-supporting activated carbon, except for drying at 130° C. for 12 hours under reduced pressure. Using the catalyst thus obtained, the reaction procedure of Example 1 was repeated.

As a result, dimethyl carbonate was obtained at a rate of 0.02 mole/h per liter of the catalyst and the methanol-based selectivity for dimethyl carbonate was 93%, and the selectivity for by-product methyl formate amounted to 6% on methanol-basis.

What is claimed is:

1. A method of producing a carbonic diester which comprises allowing an alcohol to react with carbon monoxide and oxygen in the gas phase in the presence of a catalyst containing at least one copper compound as a catalytic component selected from the group consisting of copper oxides, copper hydroxides, a salt of copper with a weak acid consisting of the elements other than halogen selected from the group consisting of a carboxylic acid, one of phenols, a metal oxo acid, carbonic acid, boric acid, hypoboric acid, peroxyboric acid and phosphoric acid, and complexes or complex salts formed with copper or a copper compound consisting of the elements other than halogen and a ligand consisting of the elements other than halogen.

2. The method of producing a carbonic diester according to claim 1 wherein the alcohol has 1 to 6 carbon atoms.

3. The method of producing a carbonic diester according to claim 1 wherein the alcohol is methanol.

4. The method of producing a carbonic diester according to claim 1, wherein the reaction is conducted in the presence of a solid catalyst.

5. The method of producing a carbonic diester according to claim 4 wherein the catalyst component is supported on a carrier selected from the group consisting of an activated carbon, alumina, silica gel, titania vanadia, and zirconia.

6. The method of producing a carbonic diester according to claim 4 wherein the reaction is conducted at a temperature of 50° to 200° C., at a pressure of 1 to 50 atm and with a space velocity of the material gas of 10 to 100,000 h$^{-1}$.

7. The method of producing a carbonic diester according to claim 4 wherein a reactant gas containing 1 to 50% by volume of the alcohol and 40 to 95% by volume of carbon monoxide based on the total volume of the alcohol, carbon monoxide and oxygen is supplied to the reaction system.

8. The method of producing a carbonic diester according to claim 4 wherein carbon monoxide is used in a proportion of 0.1 to 1,000 moles per mole of the material alcohol.

9. The method of producing a carbonic diester according to claim 4 wherein oxygen is used in a proportion of 0.001 to 2 moles per mole of the material alcohol.

10. The method of producing a carbonic diester according to claim 4 which comprises allowing the alcohol having 1 to 6 carbon atoms to react with carbon monoxide and oxygen in proportions of 0.2 to 100 moles and 0.01 to 1.5 moles respectively per mole of the material alcohol at a temperature of 50° to 200° C., at a pressure of 1 to 50 atm in the presence of the supported catalyst.

11. The method of producing a carbonic diester according to claim 10 wherein a reactant gas containing 1 to 50% by volume of the alcohol and 40 to 95% by volume of carbon monoxide based on the total volume of the alcohol, carbon monoxide and oxygen is supplied to the reaction system with a space velocity of 10 to 100,000 h$^{-1}$.

12. The method of producing a carbonic diester according to claim 11 wherein a boron-containing copper compound is used as the catalyst component of the catalyst.

13. The method of producing a carbonic diester according to claim 11 which comprises allowing methanol to react with carbon monoxide and oxygen to produce dimethyl carbonate in the presence of the catalyst wherein at least one member selected from the group consisting of cuprous hydroxide, cupric hydroxide, cuprous acetate, cupric acetate, copper metaborate, cupric borate, a complex or complex salt formed with copper or a copper compound and a boron compound consisting of the elements other than halogen is supported on an activated carbon with a specific surface area of 500 m$^2$/g or more and a mean pore size of 10 to 100 Å.

14. A method of producing a carbonic diester which comprises allowing an alcohol to react with carbon monoxide and oxygen in a liquid phase in the presence of a catalyst containing at least one member selected form the group consisting of copper metaborate, cupric borate, and a complex or a complex salt formed with (i) copper or a copper compound and (ii) a boron compound consisting of the elements other than halogen.

15. The method of producing a carbonic diester according to claim 14, wherein the alcohol has 1 to 6 carbon atoms.

16. The method of producing a carbonic diester according to claim 14, wherein the alcohol is methanol.

17. A method for producing a carbonic diester which comprises allowing an alcohol having 1 to 6 carbon atoms to react with carbon monoxide and oxygen in proportion of 0.2 to 100 moles and 0.01 to 1.5 moles respectively per mole of the alcohol in the gas phase in the presence of a catalyst which is at least one member selected from the group consisting of cupric hydroxide, cuprous hydroxide, cuprous acetate, cupric acetate, copper metaborate and cupric borate is supported on an activated carbon with a specific surface area of 700 to 3,000 m$^2$/g and a mean pore size of 10 to 100 Å in a proportion of 1 to 40% by weight based on the weight of the activated carbon at a temperature of 50 to 200° C. at a pressure of 1 to 50 atm by supplying a reactant gas containing 1 to 50% by volume of the alcohol and 40 to 95% by volume of carbon monoxide based on the total volume of the alcohol, carbon monoxide and oxygen to the reactor system with a space velocity of 10 to 100,000 h$^{-1}$.

18. A method for producing a carbonic diester which comprises allowing an alcohol having 1 to 6 carbon atoms to react with carbon monoxide and oxygen in a liquid phase in the presence of a catalyst containing at least one member selected from the group consisting of copper metaborate and cupric borate in a proportion of 0.001 to 5 g-atoms/liter in terms of atomic copper in the reaction liquid medium, at a temperature of 20° to 200° at a pressure of 1 to 200 atm at a carbon monoxide partial pressure of 0.1 to 200 atm.

* * * * *